(12) United States Patent
Fishman et al.

(10) Patent No.: US 6,432,390 B1
(45) Date of Patent: Aug. 13, 2002

(54) LOW VOC METHYL ACETATE HAIR SPRAYS

(75) Inventors: Yoram Fishman, Los Angeles; William M. Fruscella, Corona, both of CA (US)

(73) Assignee: 220 Laboratories, Riverside, CA (US)

( * ) Notice: Subject to any disclaimer, the term of this patent is extended or adjusted under 35 U.S.C. 154(b) by 0 days.

(21) Appl. No.: 09/270,640

(22) Filed: Mar. 16, 1999

(51) Int. Cl.[7] ............ A61K 7/00; A61K 9/00; A61K 31/00; A61K 47/00

(52) U.S. Cl. ............ 424/60; 424/43; 424/45; 424/47; 424/59; 424/70.1; 424/70.2; 424/70.9; 424/70.11; 424/DIG. 1; 424/DIG. 2; 514/458; 514/529; 514/546; 514/613; 514/667; 514/724; 514/727; 514/738; 514/740; 514/772; 514/785; 514/786; 514/788; 514/880; 514/974

(58) Field of Search ............ 514/458, 529, 514/546, 613, 667, 724, 727, 738, 740, 880, 974, 772, 785, 786, 788; 424/43, 45, 47, 59, 60, 70.1, 70.2, 70.9, 70.11, 70.15, 70.16, DIG. 1, DIG. 2

(56) References Cited

U.S. PATENT DOCUMENTS

| | | |
|---|---|---|
| 3,996,153 A | 12/1976 | Heeb et al. .......... 252/305 |
| 4,173,627 A | 11/1979 | Madrange nee Dermain et al. ............ 424/47 |
| 4,243,548 A | 1/1981 | Heeb et al. .......... 252/305 |
| 4,322,037 A | 3/1982 | Heeb et al. .......... 239/337 |
| 5,176,898 A | 1/1993 | Goldberg et al. ...... 424/47 |
| 5,225,190 A | 7/1993 | Halloran et al. ....... 424/70 |
| 5,374,420 A | 12/1994 | Gerstein .......... 424/70.11 |
| 5,435,993 A | 7/1995 | Hamilton et al. ...... 424/47 |
| 5,458,871 A | 10/1995 | Malawer et al. ....... 424/47 |
| 5,565,193 A | 10/1996 | Midha et al. ....... 424/70.12 |
| 5,597,551 A | 1/1997 | Malawer et al. ...... 424/47 |
| 5,614,173 A | 3/1997 | Ulmer et al. ......... 424/47 |
| 5,658,552 A | 8/1997 | Bunning et al. ....... 424/45 |
| 5,658,558 A | 8/1997 | Schwartz ......... 424/70.16 |
| 5,716,549 A | 2/1998 | Nimitz et al. ........ 252/364 |
| 5,759,522 A | 6/1998 | Ulmer et al. ......... 424/47 |
| 5,804,166 A | 9/1998 | Chan et al. .......... 424/47 |
| 5,811,109 A | 9/1998 | Cooper et al. ....... 424/401 |
| 5,830,440 A | 11/1998 | Sturla et al. ......... 424/47 |
| 5,843,881 A | 12/1998 | Dubois et al. ......... 512/1 |
| 5,853,700 A | 12/1998 | Gormley et al. ....... 424/47 |
| 5,968,495 A | * 10/1999 | Bolich, Jr. et al. .... 424/70.12 |
| 5,985,294 A | * 11/1999 | Peffly ............. 424/401 |

FOREIGN PATENT DOCUMENTS

WO 9913836 3/1999

OTHER PUBLICATIONS

The Merck Index (11th ed., 1989), pp. 73, 594, 948, 1583.*
DuPont Dymel® aerosol propellant brochure, 1995.
DuPont Dymel® aerosol propellant U.S. environmental fact sheet, 1993.

* cited by examiner

*Primary Examiner*—Jose' G. Dees
*Assistant Examiner*—Frank Choi
(74) *Attorney, Agent, or Firm*—Konrad Raynes Victor & Mann, LLP; Alan S. Raynes

(57) ABSTRACT

Embodiments relate to reduced VOC hair spray compositions. One composition includes a concentrate and propellant. The concentrate includes 25–45 weight percent alcohol, 30–50 weight percent methyl acetate, 5–15 weight percent resin, 0.2–1.3 weight percent neutralizer, and 5–25 weight percent water. The propellant comprises dimethyl ether. The composition includes 50 to 90 weight percent concentrate and 10 to 50 weight percent propellant.

27 Claims, 1 Drawing Sheet

LOW VOC METHYL ACETATE HAIR SPRAYS

TECHNICAL FIELD

Embodiments of the present invention relate to hair spray compositions. More particularly, embodiments relate to compositions having a low level of volatile organic compounds.

RELATED ART

Hair sprays are generally used to provide a temporary setting or curling effect to hair and can be removed by water or shampooing. Hair sprays typically include a hair holding agent such as a natural or synthetic resin material which is dissolved in a solvent and mixed with a propellant for delivering the product to the hair.

Typical hair holding agents include resins such as polyvinylpyrrolidone (PVP) copolymers and vinyl acetate copolymers. Typical solvents used include alcohols such as ethanol and isopropanol, which readily dissolve most resins and are compatible with a variety of propellants.

For aerosol hair sprays, hydrocarbons such as propane and butane are commonly used as propellants. Hydrocarbon propellants are useful in such compositions because they are low cost and can be liquefied under pressure. However, it is now desirable to formulate hair spray compositions with reduced levels of volatile organic compounds (VOC's), such as ethanol, isopropanol, and other volatile materials often used in aerosol products. Most hydrocarbon propellants are designated as VOC's. Recent government legislation has required that hair sprays contain reduced levels of VOC's, such as 80% or 55% VOC content. For example, to meet an 80% VOC standard, it is necessary that the ethanol and most conventional propellant components comprise no more than 80% by weight of the composition. One way to lower the VOC content is to decrease the amount of ethanol in the formulation and replace it with water.

However, there are significant problems associated with the addition of water to hair spray products. These problems may include the following: (1) a decrease in resin solubility, (2) an increase in solution viscosity, (3) excessive foaming of the composition upon discharge from the container, (4) an increase in spray particle size, which causes a poor spray pattern on the hair, (5) an increase in drying time on the hair, which also leads to a more tacky feel on the hair, (6) a decrease in holding ability as humidity increases, (7) incompatibility between the solvent (water) and the propellant, which can lead to the composition separating into two phases, and (8) corrosion of the container (typically a metal can) holding the composition. These problems are generally enhanced as the water content in the composition is increased.

Several approaches have had limited success in overcoming some of the problems described above. One approach is to use resins that are soluble or dispersible within an aqueous solvent system and then add one or more suitable polymer additives for attempting to controlling the particle size and other spray characteristics of the composition. U.S. Pat. No. 5,853,700 to Gormley, et al., discloses an aqueous hair spray formulation in which conventional polymer resins are mixed with certain polypropylene oxide-modified polydimethylsiloxane block copolymers to form a hair cosmetic composition. U.S. Pat. No. 5,176,898 to Goldberg, et al., discloses an aqueous hair spray formulation containing a volatile silicone, preferably cyclomethicone or dimethicone copolyol. These approaches, however, have not solved all of the problems noted above. For example, the combination of the volatile silicone with water and conventional propellant materials yields a product having poor spray characteristics. The interactions between the additives designed to permit the use of water, the water, and the propellant materials have led to products having less than ideal characteristics.

Another approach for forming low VOC hair sprays involves using a low or non-VOC propellant such as HFC 152a, (1,1 difluoroethane, $CHF_2CH_3$) which is sold under the trade name Dymel 152a by DuPont. HFC 152a is exempt from VOC regulations due to its low photochemical reactivity. U.S. Pat. No. 5,759,522 discloses the use of HFC 152a in combination with another propellants in order to lower the VOC content. However, 152a is very expensive, so it has not achieved wide spread use and producers would prefer to find other, less expensive ways to lower the VOC content.

SUMMARY

One embodiment of the present invention relates to a hair spray composition including a concentrate and propellant. The concentrate includes 25–45 weight percent alcohol, 30–50 weight percent methyl acetate, 5–15 weight percent resin, 0.2–1.3 weight percent neutralizer, and 5–25 weight percent water. The propellant comprises dimethyl ether. The composition includes 50 to 90 weight percent concentrate and 10 to 50 weight percent propellant.

In another aspect of embodiments of the present invention, the methyl acetate and water may together make up greater than 50 weight percent of the concentrate.

Another embodiment of the present invention includes a hair spray composition having a concentrate including 5–50 weight percent alcohol, 1–20 weight percent resin, 0.05–5.0 weight percent neutralizer, 1–50 weight percent methyl acetate, and 1–45 weight percent water. The hair spray composition includes a propellant, and the concentrate makes up approximately 50 to approximately 90 weight percent of the composition and the propellant comprises approximately 10 to approximately 50 weight percent of the composition.

Other embodiments relate to methods for manufacturing hair sprays. One such embodiment includes mixing an alcohol with a resin material to form a uniform solution. A neutralizer is mixed into the solution. Methyl acetate is mixed into the solution. Water is mixed into the solution. The solution is then combined with dimethyl ether to form a hair spray composition.

DETAILED DESCRIPTION

Figure 1:
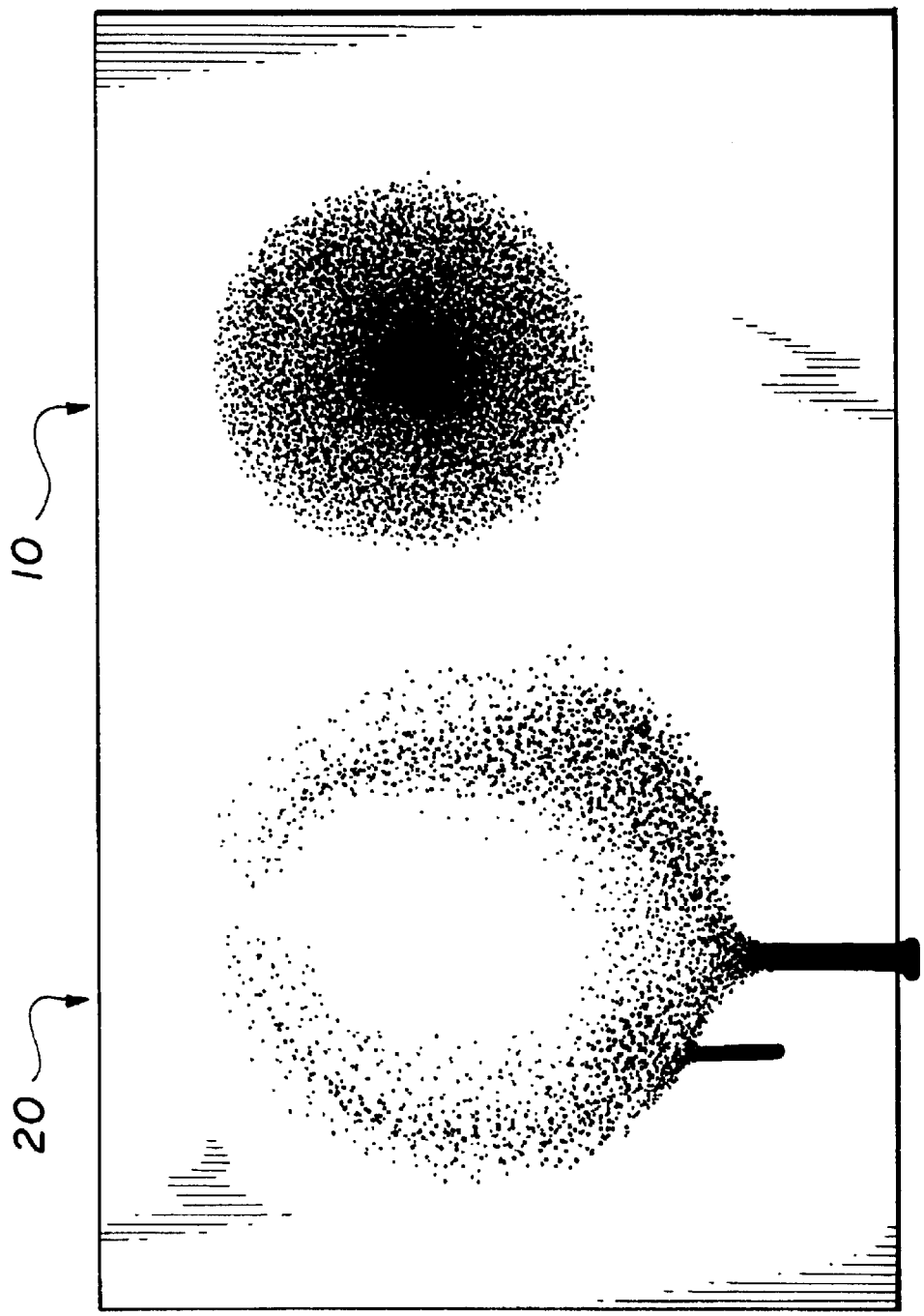
FIG. 1 illustrates spray patterns on recording paper for a 55% VOC composition containing methyl acetate and for a 55% VOC composition containing no methyl acetate.

Embodiments of the present invention include hair fixative compositions having a low VOC content. In one aspect of embodiments of the present invention, it has been found that a combination of resin, alcohol, water, methyl acetate, and dimethyl ether provides an effective hair spray formulation. If desired, other conventional additive ingredients such as conditioners, fragrances, nutrients and preservatives, may be included in the formulation. The use of methyl acetate, water and dimethyl ether permits the formulation to include a relatively small quantity of alcohol solvent and allows for the use of water or alcohol soluble additives.

One or more resin materials are used in embodiments of the present invention. Examples of resin materials which may be used include, but are not limited to, the following: (1) octylacrylamide/acrylates/butylaminoethyl methacrylate copolymer, (2) vinyl acetate/crotonic/vinyl neodecanoate copolymer, (3) butyl ester of PVA/MA copolymer (where PVA is polyvinyl acetate and MA is maleic anhydride), (4) PVP/IVA copolymer (where PVP is polyvinyl pyrrolidone and VA is vinyl acetate), (5) acrylates copolymer, (6) PVP/dimethylaminoethyl methacrylate copolymer, (7) PVP/ethyl methacrylate/methacrylic acid terpolymer, (8) methacryloyl ether betaine/acrylated copolymer, (9) sodium polystyrene sulfonate, (10) Polyquatemium 11, (12) PVP/eicosene copolymer, (13) PVP/hexadecene copolymer, and (14) VA/crotonic acid/vinyl neodecanoate copolymer. Preferred resin materials include butyl ester of PVM/MA (available under the trade name Gantrez ES-425 from ISP, Inc.), vinyl acetate/crotonic acid/vinyl neodecanoate copolymer (available under the trade name Resyn 28-2930 from National Starch & Chem. Co.), and octylacrylamide/acrylates/butylaminoethyl methacrylate copolymer. The quantity of resin in the hair spray composition may vary depending on the specific resin or resins used. Generally, embodiments include approximately 1–20 weight percent resin, more preferably approximately 5–15 weight percent.

Preferred embodiments also utilize a neutralizer material for neutralizing the resin. A variety of neutralizers could be used, including, but not limited to, aminomethyl propanol, dimethyl stearamine, triethanolamines, diethanolamines, lauramide DEA, dimethyl stearate, and ammonia. The quantity of neutralizer used is dependent on the resin it is being mixed with, and is preferably in the range of approximately 0.05–5 weight percent, more preferably approximately 0.1–2.0 weight percent, even more preferably approximately 0.2–1.3 weight percent.

A variety of solvent materials may be used in embodiments of the present invention to dissolve the resin and provides a vehicle for delivering the resin to the hair which will volatilize quickly. Preferred solvents include, but are not limited to, ethanol, 1-propanol, and 2-propanol (isopropyl alcohol). In general, the higher alcohols, such as butanol, octanol, and benzyl alcohol are not preferred due to limited solubility, odor, possible toxicity or low volatility. The quantity of alcohol solvent used may depend on the desired VOC standard to be obtained. Preferred embodiments generally include approximately 5–50 weight percent alcohol solvent. For a 55% VOC standard, more preferred embodiments include approximately 25–40 weight percent alcohol solvent.

Another component of embodiments of the present invention is methyl acetate, ($CH_3COOCH_3$) which has been found to be an effective solvent that mixes well with alcohol solvents, water and dimethyl ether to form a product having improved performance. An amount of solvent which might otherwise be a volatile alcohol can be replaced with methyl acetate (available from Hoechst-Celanese). The EPA has excluded methyl acetate as a VOC material because it has been shown to be negligibly reactive in the atmosphere. The quantity of methyl acetate may vary depending on the desired VOC standard. Preferred embodiments generally include approximately 1–50 weight percent methyl acetate. For a 55% VOC standard, more preferred embodiments include approximately 30–50 weight percent, even more preferaby approximately 35–45 weight percent.

Water is also incorporated into embodiments of the present invention. Water is not regulated as a VOC, so its use lowers the VOC content of the formulation. In addition, water may act as a solvent for certain additives and mixes well with the alcohol solvent, the methyl acetate, and the dimethyl ether to form a product having improved performance. As for the above ingredients, the quantity of water used depends on the desired VOC standard. Preferred embodiments generally include approximately 1–45 weight percent water. For a 55% VOC standard, more preferred embodiments include approximately 5–20 weight percent water.

Embodiments also include a propellant material, preferably dimethyl ether. The combination of the alcohol solvent, methyl acetate, water and dimethyl ether has been found to provide superior spraying, drying and holding characteristics on the hair. While not preferred, it is believed that a variety of other propellants could likely be used, including, for example, hydrocarbons such as butane, isobutane, propane, pentane, isopentane, HFC 152a and various combinations of these and other hydrocarbon materials. Preferred embodiments use the propellant in a quantity in the range of approximately 10–50 weight percent, more preferably approximately 25–35 weight percent, even more preferably approximately 30 weight percent. Depending on the exact propellant used, the amounts of propellant and the other ingredients could vary significantly.

Embodiments of the present invention may be formulated by adding the resin to a quantity of the alcohol solvent and stirring until the resin is dissolved. A sufficient quantity of a basic neutralizing reagent is then stirred into the mixture. The exact quantity of the base depends on the nature of the resin. Other additives may be added if desired, to impart particular properties to the composition. Examples of additives include, but are not limited to emollients, humectants, hair nutrients, rheology modifiers, anti-oxidants, fragrance, UV inhibitors, and preservatives. Water may then be added to achieve the final concentrate product volume and viscosity. The concentrate may then be combined with the desired level of propellant.

Two preferred concentrate compositions A and B for use with a propellant in a 55% VOC compliant hair spray are set forth in Tables 1 and 2 and described below.

TABLE 1

55% VOC concentrate composition A.

| Component | Weight percent |
|---|---|
| SD Alcohol 40 | 28.75 |
| butyl ester of PVM/MA copolymer | 12.5 |
| octylacrylamide/acrylates/butylaminoethyl methacrylate copolymer | 1.0 |
| dimethyl stearamine | 0.20 |
| aminomethyl propanol | 0.456 |
| methyl acetate | 40.0 |
| octyl methoxycinnamate | 0.12 |
| glycerin | 0.70 |
| panthenol | 0.02 |
| fragrance #9009 | 0.30 |
| linoleamidopropyl ethyl dimonium ethosulfate | 0.02 |
| deionized water | 15.9 |
| tocopheryl acetate | 0.01 |
| superoxide dismutase | 0.01 |
| lactamide DEA | 0.02 |

In addition to the alcohol, resins, neutralizer, methyl acetate, and water, composition A includes a variety of additives. Octylmethoxycinnamate provides sun block capabilities to the composition. Glycerin is used as an emollient and humectant. Panthenol and superoxide dismutase (available from Brooks Industries) are used as nutrients. Lactamide DEA and lineleamidopropyl ethyl dimonium ethosulfate (both available from Bernel Chemical) are surface tension modifiers, and tocopheryl acetate (available from Henkel) an antioxidant. Fragrance is used to impart a desired scent to the product. One preferred fragrance is sold by International Flavors & Fragrances as #9009.

Composition A as set forth in Table 1 may be formulated as follows. While mixing, the resins are added to the alcohol and mixing is continued to form a uniform solution. The remaining ingredients may then be added with complete mixing after the addition of each ingredient. The above steps may be performed at room temperature. The resultant product has a pH of approximately 6.5 and a specific gravity of approximately 0.923. The product may then be mixed with a propellant. One preferred propellant is dimethyl ether. The preferred propellant to concentrate ratio when using dimethyl ether is 30% propellant to 70% concentrate.

TABLE 2

55% VOC concentrate formulation B.

| Component | Weight percent |
| --- | --- |
| SD Alcohol 40 | 35.0 |
| vinyl acetate/crotonic acid/vinyl neodecanoate copolymer | 9.00 |
| aminomethyl propanol | 0.90 |
| dimethicone copolyol | 0.30 |
| panthenol | 0.03 |
| glycerin | 0.50 |
| octyl methoxycinnamate | 0.05 |
| methyl acetate | 43.9 |
| fragrance | 0.30 |
| deionized water | 10.00 |
| tocopheryl acetate | 0.01 |

Composition B as set forth in Table 2 may be formulated in the same manner as described above for composition A. In addition to some of the same ingredients as composition A, composition B also includes additives including dimethicone copolyol (available from Dow Corning) is to enhance shine and as a rheology modifier to improve flow properties of the composition. The resultant product has a pH of approximately 8.3 and a specific gravity of approximately 0.907.

Experimental tests were performed to compare the drying time and atomization characteristics of 55% VOC formulations according to compositions A and B described above of the present invention, containing methyl acetate and dimethyl ether, versus other 55% VOC formulations containing no methyl acetate and no dimethyl ether. These other formulations were provided by National Starch and Chemical Corp. as representative of the current industry 55% VOC standard and contained HFC 152a as the propellant. The containers were sprayed onto a spray substrate (Sanborn Recording Permapaper) from a distance of approximately 12 inches. The nozzles were kept perpendicular and the spray discharged from each container for approximately 5–10 seconds. The time to achieve a totally tack free film using cotton gauze was recorded. The overall appearance of the resultant film was evaluated.

The results indicated that the formulations including methyl acetate afforded superior atomization of the spray mist, resulting in a finer particle size. Formulations without methyl acetate produced excessive running and pooling of the film, in addition to marked differences in the uniformity of the spray patterns. The methyl acetate formulations also provided considerably faster drying films, averaging about 2 to 3 times faster for measurements of the time for the spray pattern to have a complete loss of tackiness. An example of one of the tests is provided in FIG. 1, which shows two spray patterns 10 and 20 on the recording paper. Pattern 10 is from a 55% VOC formulation having methyl acetate, and pattern 20 is from the 55 percent VOC formulation having no methyl acetate. The sprays were discharged for approximately 8 seconds. As can be seen, the spray pattern for the pattern 10 containing methyl acetate appears to have a finer particle size and is more uniform than the spray pattern for the pattern 20. In addition, the pattern 10 dried in a substantially more uniform manner, unlike the pattern 20, which showed excessive running during drying.

Preferred embodiments of the present invention offer a high performance 55% VOC standard hair spray which can be manufactured relatively inexpensively. Instead of a composition including a large quantity of alcohol and thus requiring the use of an expensive non-VOC propellant (HFC 152a) to meet the 55% VOC standard, embodiments of the present invention utilize a combination of methyl acetate, alcohol and water to lower the VOC content and then mix the combination with dimethyl ether (which is significantly less expensive than HFC 152a) to form a hair spray having desirable properties.

It will, of course, be understood that modifications of the present invention, in its various aspects, will be apparent to those skilled in the art. The scope of the invention should not be limited by the particular embodiments described above. Other embodiments are also possible, their specific features depending upon the particular application. For example, embodiments of the present invention may be applicable to a variety of non-aerosol hair sprays by the elimination of the propellant.

In addition, it should be noted that the classification of ingredients in compositions such as cosmetics may be somewhat arbitrary. For example, propylene glycol may be classified as both a humectant and as a viscosity modifier. Consequently, for purposes of the descriptions herein, the components are characterized according to what is believed to be their primary roles in providing the desired properties as used in compositions as described above.

What is claimed is:
1. A hair spray composition comprising a concentrate and propellant:
   wherein the concentrate comprises:
      25–45 weight percent alcohol;
      30–50 weight percent methyl acetate;
      5–15 weight percent resin;
      0.2–1.3 weight percent neutralizer; and
      5–25 weight percent water;
   wherein the propellant comprises dimethyl ether; and
   wherein the composition includes 50 to 90 weight percent concentrate and 10 to 50 weight percent propellant.

2. A hair spray composition as in claim 1, wherein the methyl acetate and water make up at least 50 weight percent of the concentrate.

3. A hair spray composition as in claim 2, wherein the concentrate comprises approximately 10 to approximately 20 weight percent water.

4. A hair spray composition as in claim 3, wherein the concentrate comprises approximately 35 to approximately 45 weight percent methyl acetate.

5. A hair spray composition as in claim 4, wherein the concentrate comprises approximately 30 to approximately 40 weight percent alcohol.

6. A hair spray composition as in claim 5, wherein the concentrate comprises approximately 9 to approximately 13 weight percent resin.

7. A hair spray composition as in claim 6, comprising approximately 25 to approximately 35 weight percent propellant.

8. A hair spray composition as in claim 6, wherein the neutralizer comprises amino methyl propanol and the resin comprises butyl ester of polyvinyl acetate and maleic anhydride.

9. A hair spray composition as in claim 1, the hair spray having a VOC content of no greater than 55%, comprising:
   a concentrate comprising:
      25–44 weight percent alcohol;
      30–50 weight percent methyl acetate;
      5–15 weight percent resin;
      0.2–1.3 weight percent neutralizer; and
      5–25 weight percent water;
   a propellant comprising dimethyl ether;
   wherein the composition includes 60 to 80 weight percent concentrate and 20 to 40 weight percent propellant.

10. A hair spray composition as in claim 1, wherein the concentrate further comprises:
   at least 0.01 percent by weight glycerin;
   at least 0.01 percent by weight panthenol;
   at least 0.01 percent by weight octyl methoxycinnamate; and
   at least 0.005 percent by weight tocoheryl acetate.

11. A hair spray composition as in claim 10, wherein the concentrate further comprises at least one fragrance.

12. A hair spray composition as in claim 1, wherein the concentrate has a pH in the range of 6 to 7.

13. A hair spray composition as in claim 1, wherein the concentrate has a pH in the range of 8 to 9.

14. A hair spray composition as in claim 1, wherein the concentrate has a specific gravity in the range of 0.900 to 0.950.

15. A hair spray composition comprising:
   a concentrate comprising:
      approximately 25 to approximately 35 weight percent alcohol;
      approximately 35 to approximately 45 weight percent methyl acetate;
      approximately 5 to approximately 15 weight percent resin;
      approximately 0.2 to approximately 1.3 weight percent neutralizer; and
      approximately 9 to approximately 20 weight percent water;
   a propellant comprising dimethyl ether;
   the concentrate comprising approximately 60 to approximately 80 weight percent of the hair spray composition; and
   the propellant comprising approximately 20 to approximately 40 weight percent of the hair spray composition.

16. A hair spray composition as in claim 15, wherein the water and methyl acetate together make up greater than 50 weight percent of the concentrate.

17. A hair spray composition comprising:
   25–45 weight percent alcohol;
   5–15 weight percent resin;
   0.2–1.3 weight percent neutralizer;
   30–50 weight percent methyl acetate; and
   5–25 weight percent water.

18. A hair spray composition as in claim 17, wherein the methyl acetate and water make up at least 50 weight percent of the composition and the methyl acetate is present in an amount of from 35 to 45 weight percent of the composition.

19. A hair spray composition as in claim 17, wherein the methyl acetate and water make up at least 50 weight percent of the composition.

20. A hair spray composition as in claim 17, wherein the neutralizer comprises amino methyl propanol and the resin comprises butyl ester of polyvinyl acetate and maleic anhydride.

21. A hair spray composition as in claim 20, further comprising:
   at least 0.01 percent by weight glycerin;
   at least 0.01 percent by weight panthenol;
   at least 0.01 percent by weight octyl methoxycinnamate; and
   at least 0.005 percent by weight tocopheryl acetate.

22. A hair spray composition as in claim 17, wherein the composition comprises approximately 10 to approximately 20 weight percent water.

23. A hair spray composition as in claim 17, wherein the composition comprises approximately 35 to approximately 45 weight percent methyl acetate.

24. A hair spray composition as in claim 17, wherein the composition comprises approximately 9 to approximately 13 weight percent resin.

25. A hair spray composition as in claim 17, wherein the composition does not include a polysiloxane component.

26. A hair spray composition as in claim 25, further comprising a propellant.

27. A hair spray composition consisting essentially of:
   25–45 weight percent alcohol;
   30–50 weight percent methyl acetate;
   5–15 weight percent resin;
   0.2–1.3 weight percent neutralizer; and
   5–25 weight percent water.

* * * * *